US012594106B1

(12) United States Patent
Mitchell

(10) Patent No.: US 12,594,106 B1
(45) Date of Patent: Apr. 7, 2026

(54) CABLE PASSER FOR FIXING FRACTURES

(71) Applicant: Joseph Mitchell, San Diego, CA (US)

(72) Inventor: Joseph Mitchell, San Diego, CA (US)

( * ) Notice: Subject to any disclaimer, the term of this patent is extended or adjusted under 35 U.S.C. 154(b) by 0 days.

(21) Appl. No.: 18/813,393

(22) Filed: Aug. 23, 2024

Related U.S. Application Data

(60) Provisional application No. 63/540,166, filed on Sep. 25, 2023.

(51) Int. Cl.
*A61B 17/82* (2006.01)
*A61B 17/88* (2006.01)

(52) U.S. Cl.
CPC .......... *A61B 17/8861* (2013.01); *A61B 17/82* (2013.01)

(58) Field of Classification Search
CPC ... A61B 17/0469; A61B 17/82; A61B 17/823; A61B 17/84; A61B 17/842; A61B 17/88; A61B 17/8861; A61B 2017/0472
See application file for complete search history.

(56) References Cited

U.S. PATENT DOCUMENTS

| | | | | |
|---|---|---|---|---|
| 4,312,337 A * | 1/1982 | Donohue | ........... | A61B 17/1796 606/103 |
| 4,606,335 A * | 8/1986 | Wedeen | ................ | A61B 17/04 606/103 |
| 5,772,663 A * | 6/1998 | Whiteside | .............. | A61B 17/82 606/103 |
| 7,942,878 B2 * | 5/2011 | Fernandez | ......... | A61B 17/8861 606/103 |
| 8,579,900 B2 * | 11/2013 | Hsu | ........................ | A61B 17/82 606/139 |
| 10,258,401 B2 * | 4/2019 | Fallin | ................. | A61B 17/1778 |
| 10,314,628 B2 * | 6/2019 | Dooney | ................. | A61B 17/06 |
| 11,771,416 B2 * | 10/2023 | Dooney, Jr. | ........ | A61B 17/0401 606/144 |
| 12,082,861 B2 * | 9/2024 | Choudhury | ........ | A61B 17/8861 |
| 12,402,926 B2 * | 9/2025 | Denard | ................. | A61B 17/82 |
| 2004/0204717 A1 * | 10/2004 | Fanger | .............. | A61B 17/1757 606/96 |
| 2006/0293691 A1 * | 12/2006 | Mitra | ................. | A61B 17/8861 606/103 |
| 2007/0043377 A1 * | 2/2007 | Fernandez | ............. | A61B 17/82 606/103 |
| 2007/0088362 A1 * | 4/2007 | Bonutti | ............... | A61F 2/30749 606/99 |
| 2009/0306668 A1 * | 12/2009 | Dell'Oca | ........... | A61B 17/8861 606/74 |
| 2010/0198235 A1 * | 8/2010 | Pierce | ................ | A61B 17/0469 606/148 |
| 2011/0166574 A1 * | 7/2011 | Hsu | .................... | A61B 17/8861 606/74 |

(Continued)

FOREIGN PATENT DOCUMENTS

| | | | | | |
|---|---|---|---|---|---|
| CN | 113679465 A | * | 11/2021 | ............. | A61B 17/88 |
| WO | WO-2023018890 A1 | * | 2/2023 | ......... | A61B 17/8869 |

*Primary Examiner* — Eric S Gibson

(74) *Attorney, Agent, or Firm* — Plager Schack LLP; Mark H. Plager; Kara K. Verryt

(57) ABSTRACT

A cable passer for passing multiple cerclage cables simultaneously when fixing a bone fracture may include a handle; an arm extending from the handle; and a slot tube attached to a distal end of the art, the slot tube having a concavely curved shape, wherein the slot tube includes a plurality of channels having at least a first channel and a second channel extending therethrough.

7 Claims, 3 Drawing Sheets

(56)             References Cited

U.S. PATENT DOCUMENTS

| | | | |
|---|---|---|---|
| 2014/0249530 A1* | 9/2014 | Babikian | A61B 17/8861 |
| | | | 606/74 |
| 2017/0265918 A1* | 9/2017 | Dooney | A61B 17/04 |
| 2018/0153603 A1* | 6/2018 | Songer | A61B 17/8861 |
| 2021/0346073 A1* | 11/2021 | Choudhury | A61B 17/82 |
| 2022/0015756 A1* | 1/2022 | Dooney, Jr. | A61F 2/0805 |
| 2022/0273349 A1* | 9/2022 | Denard | A61B 17/842 |
| 2023/0346443 A1* | 11/2023 | Lindvall | A61B 17/82 |

* cited by examiner

CABLE PASSER FOR FIXING FRACTURES

RELATED APPLICATION

This application claims priority to provisional patent application U.S. Ser. No. 63/540,166 filed on Sep. 25, 2023, the entire contents of which is herein incorporated by reference.

BACKGROUND

The embodiments herein relate generally to medical devices, and more particularly, to a cable passer for fixing fractures, wherein the cable passer provides for the passing of multiple cerclage cables simultaneously.

Fixing fractures, such as long bone fractures, often requires passing, tightening, and securing multiple cerclage cables around the bone. However, conventional cable passers only allow a surgeon or medical professional to pass one cable at a time. As such, each cerclage cables must be individually passed, tightened, and secured, thus increasing the risk of patient harm, such as injury to vessels, nerves, or the like, and increasing the time required to complete the surgery. It is well known that shortened surgery times can provide for more beneficial outcomes, such as reduced infections rates and reduced blood loss.

Therefore, what is needed is a device that provides for the passing of multiple cerclage cables simultaneously, thus increasing efficiency and decreasing risk of patient harm when fixing a long bone fracture. More specifically, passing multiple cerclage cables simultaneously may lower the risk of iatrogenic (physician related) injury by reducing the number of times a surgeon must pass the cable around a broken bone, as each pass can result in injury.

SUMMARY

Some embodiments of the present disclosure include a cable passer for passing multiple cerclage cables simultaneously when fixing a bone fracture. The cable passer may include a handle; an arm extending from the handle; and a slot tube attached to a distal end of the art, the slot tube having a concavely curved shape, wherein the slot tube includes a plurality of channels having at least a first channel and a second channel extending therethrough.

BRIEF DESCRIPTION OF THE FIGURES

The detailed description of some embodiments of the invention is made below with reference to the accompanying figures, wherein like numerals represent corresponding parts of the figures.

DETAILED DESCRIPTION

In the following detailed description of the invention, numerous details, examples, and embodiments of the invention are described. However, it will be clear and apparent to one skilled in the art that the invention is not limited to the embodiments set forth and that the invention can be adapted for any of several applications.

The device of the present disclosure may be used as a cable passer for passing multiple cerclage cables simultaneously when fixing a fractured bone and may comprise the following elements. This list of possible constituent elements is intended to be exemplary only, and it is not intended that this list be used to limit the device of the present application to just these elements. Persons having ordinary skill in the art relevant to the present disclosure may understand there to be equivalent elements that may be substituted within the present disclosure without changing the essential function or operation of the device.

The various elements of the present disclosure may be related in the following exemplary fashion. It is not intended to limit the scope or nature of the relationships between the various elements, and the following examples are presented as illustrative examples only.

Figures 1, 2:
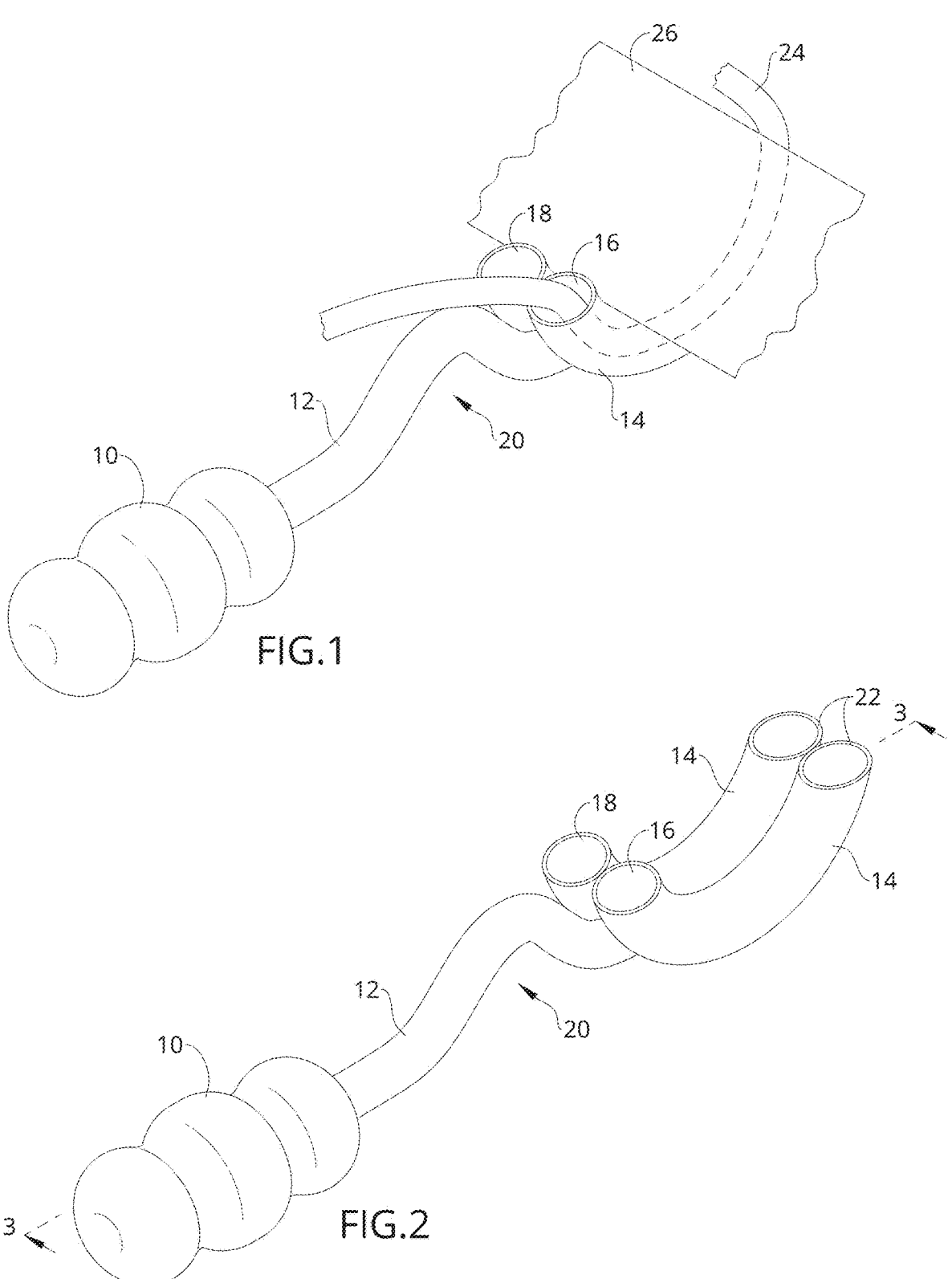
FIG. 1 is a perspective view of one embodiment of the present disclosure, shown in use.
FIG. 2 is a perspective view of one embodiment of the present disclosure.
Figure 3:
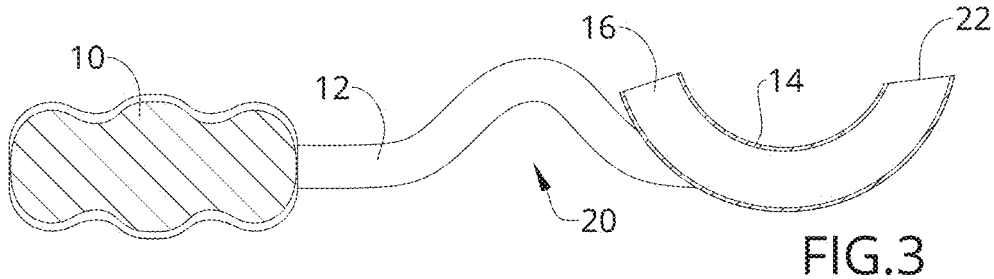
FIG. 3 is a section view of one embodiment of the present disclosure, taken along line 3-3 in FIG. 2.
Figure 4:
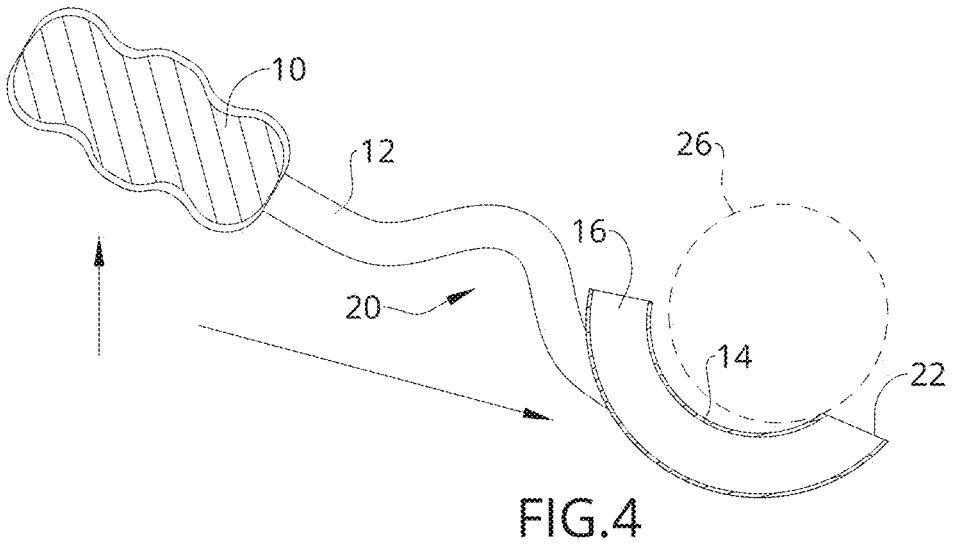
FIG. 4 is a section view of one embodiment of the present disclosure, showing motion of use.
Figure 5:
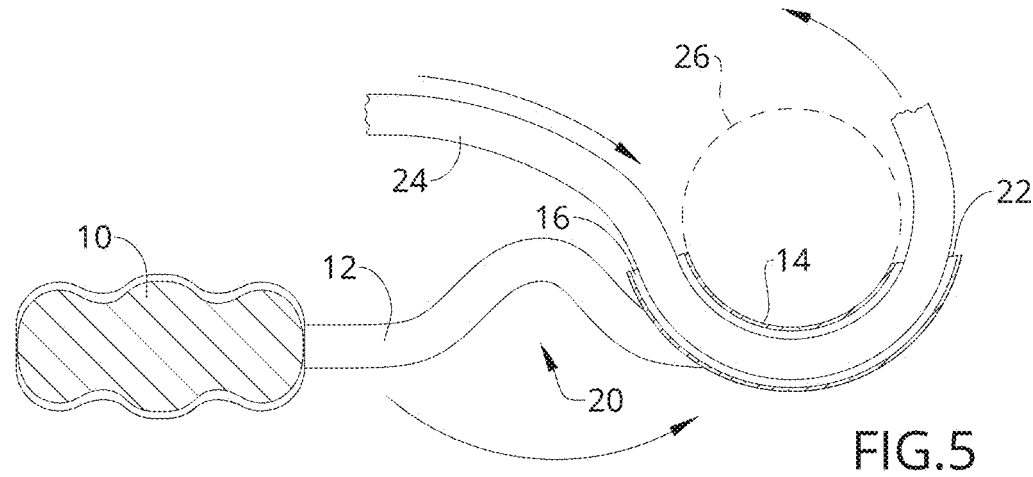
FIG. 5 is a section view of one embodiment of the present disclosure, showing motion.

By way of example, and referring to FIG. 1-6, some embodiments of the present disclosure include a cable passer for passing multiple cerclage cables 24 simultaneously when fixing a fractured bone 26, the cable passer comprising a handle 10, an arm 12 extending from the handle 10, and slot tube 14 attached to a distal end of the arm, wherein the slot tube 12 includes at least a first channel 16 and a second channel 18 extending therethrough, the slot tube 14 having a substantially curved shape. For example, as shown in the Figures, the curve of the slot tube 14 may be a concave curve. As shown in FIG. 1, the curvature of the slot tube 14 may be suitable for accommodating placement of a fractured bone 26 therein.

More specifically, and as shown in FIGS. 1-6, the handle 10 may comprise a handle suitable for being gripped by a surgeon or similar medical professional. The handle 10 may have an ergonomic structure, such as that shown in the Figures, but the use of other shaped handles is also envisioned. In fact, the shape of the handle 10 on a particular cable passer may depend on the preferences of the user and, as such, many variations of the cable passer with varying handles 10 may exist. However, in any case and as shown, the handle 10 may be attached to a proximal end of the arm 12.

In embodiments, the arm 12 may comprise a rod-like member, wherein a proximal end of the arm 12 is attached to the handle 10 and a distal end of the arm 12 may be attached to the slot tube. In some embodiments, the arm 12 may include a recess curve 20 built therein, such that the arm 12 is not simply a planar or straight rod, wherein the recess curve 20 may curve in the opposite direction as the curve of the slot tube 14. In a particular embodiment, the arm 12 may be a sole rod-like member. In other embodiments, the arm 12 may have varying curvatures or structures, depending on the fractured bone 26 to be accessed and fixed.

As shown in FIGS. 1-5, the slot tube 14 may comprise a substantially curved tubular member with a first channel 16 and a second channel 18 extending therethrough. The channels 16, 18 may run substantially parallel to the elongate length of the arm 12, such that the inlet opening to each of the channels 16, 18 is proximate to the distal end of the arm 12 and the outlet opening 22 for each of the channels 16, 18 is positioned away from the distal end of the arm 12. As shown in FIGS. 1-5, the slot tube 14 may comprise a plurality of individual curved tube members attached to and aligned with one another to form the overall slot tube structure with parallel channels. While FIGS. 1-5 show the slot tube 14 having two curved members, the slot tube 14 is not limited to only having two curved tube members. As long as the slot tube 14 comprises at least two channels, the cable passer may be configured to provide for the passing of at least two cerclage cables 24 during use. In fact, in other embodiments, the slot tube 14 may comprise more than two channels by attaching additional curved tube members together.

Figure 6:
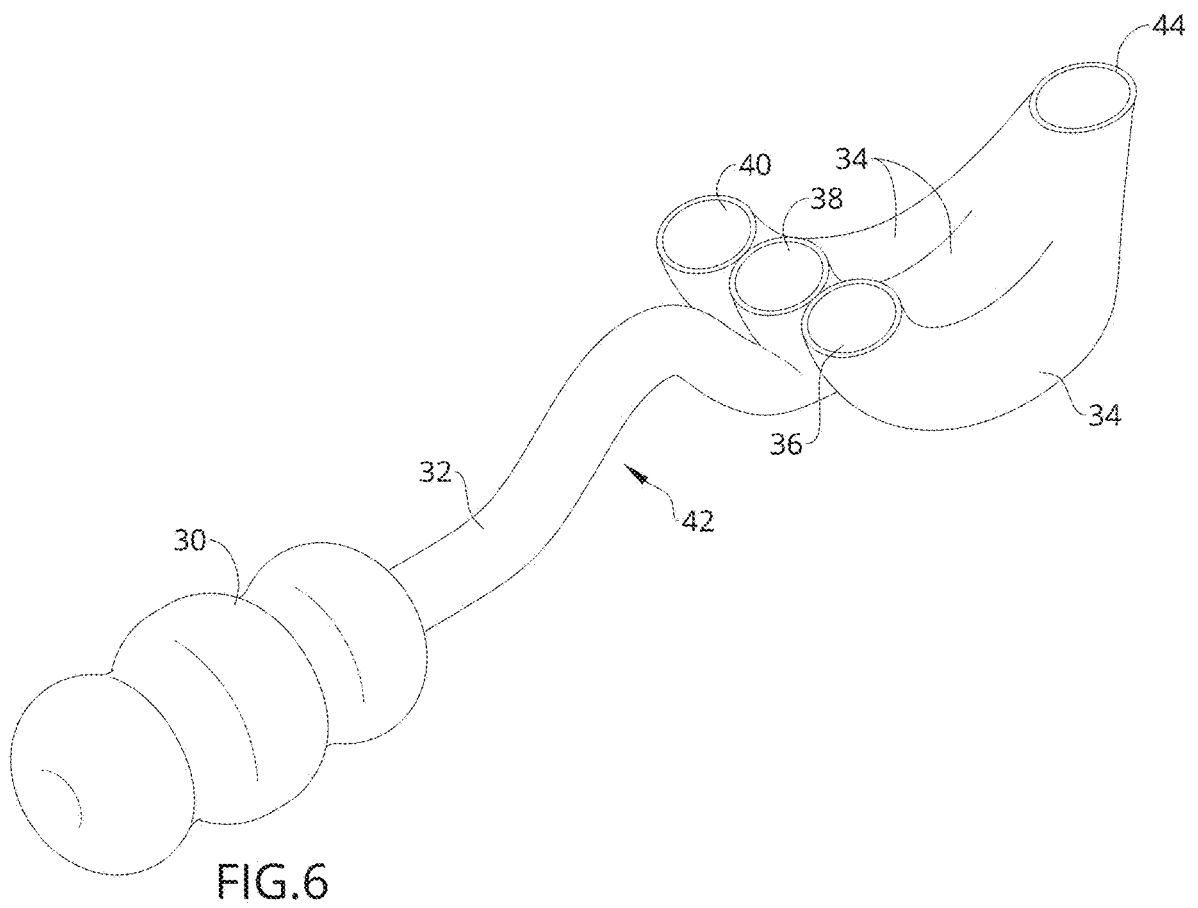
FIG. 6 is a perspective view of one embodiment of the present disclosure.

Alternatively, and as shown in FIG. 6, the cable passer may comprise a handle 30, an arm 32, optionally with a recess curve 42, and a multi-slot tube 34 attached to a distal end of the arm 32. The handle 30 and arm 32 may be similar to the handle 10 and arm 12, as described in detail above, but the multi-slot tube 34 may have a structure that varies slightly from that of the slot tube 14. As shown, the multi-slot tube 34 may still comprise multiple channels extending therethrough, such as first channel 36, second channel 38, and third channel 40, but the channels 36, 38, 40 may converge to a single outlet 44. In fact, this alternate version of the cable passer may include two or more channels that merge to a single outlet 44. The number of channels that converge is not particularly limited, so long as there are at least two channels to provide for the passing of at least two cables 24.

The cable passer of the present disclosure may be made of any suitable materials and, in some embodiments, the handle may comprise wood or plastic, the arm may comprise a curved, solid, metal or plastic arm, and the slot tube may comprise a hollow metal or plastic cable passageway. However, the use of other rigid materials is envisioned for the arm and the slot tube, and the handle may be made from any suitable and desired material. As mentioned above, the slot tube may include at least two passageways for cables 24, which may either converge to a single outlet or each have their own outlet. In some embodiments, the outlet opening may be beveled.

To use the cable passer of the present disclosure, the surgeon may first expose the fractured bone 26 that is to be cabled, fixed, or reduced. A provisional reduction (alignment) of the fracture may be routinely performed. The slot tube, which is in the shape of a curved hook, may then be passed around the fracture by manipulating the handle. Once the slot tube is around the fracture, the cables 24 may then be passed by being placed into the opening(s) of the slot tube that is furthest away from the surgeon until they exist the closer/nearer portion of the slot. The slot tube may then be extracted, leaving the cables 24 behind. A different device, which already exists, may then be used to tighten and secure the cables. Because the cable passer of the present disclosure allows multiple cables 24 to be passed simultaneously, the surgeon may not have to repeat the process over and over, thus reducing the time need and the risk of harm to the patient.

The above-described embodiments of the invention are presented for purposes of illustration and not of limitation. While these embodiments of the invention have been described with reference to numerous specific details, one of ordinary skill in the art will recognize that the invention can be embodied in other specific forms without departing from the spirit of the invention. Thus, one of ordinary skill in the art would understand that the invention is not to be limited by the foregoing illustrative details, but rather is to be defined by the appended claims.

What is claimed is:

1. A cable passer for passing multiple cerclage cables simultaneously when fixing a bone fracture, the cable passer comprising:
   a handle;
   an arm extending from the handle, the arm comprising:
      a first elongate portion;
      a distal end aligned with the first elongate portion; and
      a curved portion positioned between the elongate portion and the distal end; and
   a slot tube attached to a distal end of the arm, the slot tube having a concavely curved shape,
   wherein:
      the slot tube comprises a plurality of individually curved members directly attached to, aligned with, and directly abutting one another;
      the slot tube includes a plurality of channels comprising at least a first channel and a second channel extending therethrough; and
      the curved portion of the arm includes a recess curve that curves away from and back to a linear plane of the elongate portion and the distal end.

2. The cable passer of claim 1, wherein the plurality of channels each run substantially parallel to an elongate length of the arm, such that an inlet opening to each channel of the plurality of channels is proximate to the distal end of the arm and an outlet opening for each of the plurality of channels is positioned away from the distal end of the arm.

3. The cable passer of claim 2, wherein each member of the plurality of individually curved members comprises its own respective channel extending therethrough, thus forming a slot tube structure with parallel channels.

4. The cable passer of claim 1, wherein the slot tube comprises three channels.

5. The cable passer of claim 1, wherein the arm comprises an elongate tube.

6. The cable passer of claim 5, wherein the recess curve curves in an opposite direction of the slot tube.

7. A cable passer for passing multiple cerclage cables simultaneously when fixing a bone fracture, the cable passer comprising:
   a handle;
   an arm extending from the handle; and
   a slot tube attached to a distal end of the arm, the slot tube having a concavely curved shape,
   wherein:
      the slot tube comprises a multi-slot tube comprising multiple channels extending therethrough;
      each channel of the multiple channels has its own distinct opening, wherein the openings are separated from each other by a structural wall of the slot tube; and
      the multiple channels converge to a single outlet.

* * * * *